United States Patent [19]

Freedman et al.

[11] Patent Number: 5,670,521
[45] Date of Patent: Sep. 23, 1997

[54] REVERSAL OF MULTI-DRUG RESISTANCE BY TRIPHENYL-AZACYCLOALKANE DERIVATIVES

[75] Inventors: Jules Freedman, Cincinnati, Ohio; Sai P. Sunkara, Mercer Island, Wash.

[73] Assignee: Merrell Pharmaceuticals Inc., Cincinnati, Ohio

[21] Appl. No.: 583,196

[22] Filed: Jan. 4, 1996

Related U.S. Application Data

[63] Continuation of Ser. No. 284,532, filed as PCT/US93/00669, Jan. 11, 1993 published as WO93/16044, Aug. 19, 1993, abandoned.

[51] Int. Cl.$^6$ ................................................. A01K 31/445
[52] U.S. Cl. ......................................................... 514/317
[58] Field of Search ............................................. 514/317

[56] References Cited

U.S. PATENT DOCUMENTS

| | | | |
|---|---|---|---|
| 2,898,339 | 8/1959 | Wheeler et al. | 260/293.4 |
| 3,956,296 | 5/1976 | Duncan et al. | 260/297.2 A |
| 4,035,372 | 7/1977 | Deason et al. | 260/293.77 |
| 4,851,423 | 7/1989 | Girijavallab-han et al. | 514/399 |
| 4,990,511 | 2/1991 | Nakajima et al. | 514/255 |

FOREIGN PATENT DOCUMENTS

| | | | |
|---|---|---|---|
| 0235463 | 9/1987 | European Pat. Off. | 546/210 |
| 0467435 | 1/1992 | European Pat. Off. | 546/210 |
| 0471612 | 2/1992 | European Pat. Off. . | |
| 1188403 | 9/1959 | France | 546/210 |
| 9015599 | 12/1990 | WIPO | 546/210 |
| 9110651 | 7/1991 | WIPO | 546/210 |
| 9316044 | 8/1993 | WIPO . | |

OTHER PUBLICATIONS

Kartner et al, *Scientific American*, pp. 44–51, Mar. 1989.
Tsuruo, et al, *Cancer Research*, 43, pp. 2905–2910, Jun. 1983.
Helson, *Cancer Drug Delivery*, vol. 1, No. 4, pp. 353–361, (1984).
Tsuruo et al, *Cancer Research*, 43, pp. 2267–2272, May 1983.
Gottesman et al, *TIPS* vol. 9, pp. 54–58, Feb. 1988.
Fields et al, *Nature*, vol. 333, pp. 278–280, (1988).
Chemical Abstracts, vol. 102:45760p, (1985).
Liu–Hong et al, *Yaoxue Xuebao*, 19(9) pp. 671–675, 198.
Chemical Abstracts vol. 102, No. 2490f Xuebao, 1984, pp. 171–175, "Piperthy 4–(2, 2–dipheriylethyl)–1–(phenylmethal)–, hydrochloride".
Endicott et al, *Annu. Rev. Biochem.* vol. 58, 1989, pp. 137–171 "The Bio–chemistry of P–glycoprotein–mediated Multidrug Resistance".
Ford, *Pharmacological Reviews*, vol. 42, No. 3, 1990, pp. 155–199, "Pharmacology of drugs that alter multidrug resistance in cancer".
Wu, et al, *Cancer Research*, 52, pp. 3029–3034, Jun. 1, 1992.
Chemical Abstracts, vol. 67,32621c, 1967.

*Primary Examiner*—C. Warren Ivy
*Assistant Examiner*—Raymond Covington
*Attorney, Agent, or Firm*—William R. Boudreaux

[57] ABSTRACT

Certain triphenylpiperidines reverse drug resistance in multi-drug resistant tumors. These compounds apparently function by inhibiting a p-glycoprotein pump which becomes activated in late stage tumor development and which is inherently present in tumors from certain origins.

4 Claims, No Drawings

REVERSAL OF MULTI-DRUG RESISTANCE BY TRIPHENYL-AZACYCLOALKANE DERIVATIVES

CROSS-REFERENCE TO RELATED APPLICATION

This is a continuation of application Ser. No. 08/284,532, filed Aug. 5, 1994 now abandoned which is a national phase filing of PCT/0593/00669 filed Jan. 11, 1993 published as WO93/16044, Aug. 19, 1993.

Effective tumor treatment is frequently thwarted by the lack of sensitivity of certain tumors to standard chemotherapeutic agents (intrinsic resistance) or by the ability of certain tumors to develop a lack of chemotherapeutic sensitivity during the course of treatment (acquired or extrinsic resistance). The cause of these phenomena has been linked to the existence of an energy-dependent efflux pump which acts to remove the chemotherapeutic agent from the target cell. The pump consists of the P-glycoprotein found as a constituent of cell membrane, and it has been suggested that the normal function of the P-glycoprotein is to remove toxins from within the cell. This theory is supported by the observation that P-glycoprotein is found as a cell membrane constituent in cells such as liver, kidney, colon, and jejunum. It has been suggested that P-glycoprotein in the cell membrane of such normal tissues could act to remove toxins or to assist in the transport of nutrients and solutes and in secreting a variety of protein and steroid substances. Natural presence of P-glycoprotein in tumor cells derived from these tissues as well as its presence in tumor cells derived from other tissue types could explain, at least in part, resistance of various tumors to therapy with standard chemotherapeutic agents.

Disubstituted piperidine and pyrrolidine derivatives have already been disclosed in the art. In this respect, reference may be made to the following documents:

WO 91/10651 which relates to certain disubstituted piperidine and pyrrolidine derivatives useful as selective muscarinic receptor antagonists;

EP-A2-0235463 which relates to certain N-substituted arylalkyl and arylalkylenepyrrolidines, peperidines and homopiperidines useful in methods of treating cardiovascular dysfunctions, countering the effects of histamine in allergies and countering gastric secretion excesses;

FR-A1-188403 which relates to certain disubstituted piperidine derivatives;

Acta Pharmaceutica Sinica, vol. 19, 671–675 (1984) which relates to the synthesis of 2',2'-diphenylethylazacycloalkane derivatives and their uses as anticholinergics.

There are also many multidrug resistance reversing agents and anti-neoplastic enhancing agents known in the art. Hence, reference may be made to the following documents:

WO-A-90/15599 which relates to the use of certain aryl-substituted amine derivatives as adjuvant chemotherapy for neoplasias resistant to multiple drugs;

EP-A3-0467435 which relates to the use of certain benzylhydryl derivatives useful for the treatment of patients suffering from calmodulin-influenced diseases;

Annu. Rev, Biochem, 58, 137–171 (1989) which relates the biochemistry of P-glycoprotein-mediated multidrug resistance;

Pharmacol. Rev., 42, 155–199 (1990) which relates to the pharmacology of drugs that alter multidrug resistance in cancer.

The use of additional therapeutic agents which inactivate the P-glycoprotein pump would be invaluable in the treatment of multidrug resistant tumors.

SUMMARY OF THE INVENTION

Compounds of formula $$\begin{array}{c} \text{piperidine ring with } (CH_2)_m \text{ bridge, } -(CH_2)_q\text{CH}(Ph_2)(Ph_3) \text{ substituent, and } N-(CH_2)_n-Ph_1 \end{array} \qquad 1$$

wherein $Ph_1$, $Ph_2$, and $Ph_3$ are each a phenyl group optionally substituted with up to a combination of three members of the group consisting of F, Br, Cl, OH, $CF_3$, $NH_2$, $N(CH_3)_2$, $(C_{1-4})$alkyl, $(C_{1-4})$alkoxy, and $(C_{1-4})$alkylthio;

n is an integer of from 1 to 5;

m is 0 or an integer of from 1 to 2; and q is an integer of from 1 to 2;

or an acid addition salt thereof reverse multidrug resistance in multidrug resistant tumor cells and are thus useful adjuvants in the treatment of tumors.

DETAILED DESCRIPTION OF THE INVENTION

This invention relates to the compounds of Formula 1 as well as their use as agents effective in reversing drug resistance in multi-drug resistant tumors. The compounds of formula 1 can be administered together with standard chemotherapeutic agents, can be used in the treatment of tumors which are intrinsically or extrinsically multi-drug resistant, and can be used to reverse resistance in experimental multi-drug resistant tumor cell lines. Multi-drug resistance is defined to be that condition of a tumor cell in which the cell is resistant to a wide variety of unrelated anti-cancer drugs such as vinca alkaloids, epipodophyllotoxins, dactinomycin, and anthracycline classes as well as colchicine. (Goodman and Gilman, 7th Ed., p. 1278). This broad based, cross-resistance can develop after administration of a single agent of either the vinca alkaloid, epipodophyllotoxins, dactinomycin, and anthracycline classes as well as colchicine and is characterized by resistance to the other members of these drug classes. Examples of anti-tumor drugs of the vinca alkaloid class include the naturally occurring vincristine and vinblastine as well as the synthetic derivative vindesine. Examples of anti-tumor drugs of the epipodophyllotoxins class include etoposide and teniposide. Example of anti-tumor drugs of the anthracycline class is daunorubicin. An example of an anti-tumor drugs of the dactinomycin class include actinomycin A and actinomycin D.

As used herein, the term "$(C_{1-4})$alkoxy" means a straight or branched chain alkoxy group having from one to four carbon atoms such as methoxy, ethoxy, n-propoxy, isopropoxy, n-butoxy, isobutoxy, sec-butoxy, tert-butoxy.

The compounds of Formula 1 may contain one or more asymmetric centers and may therefore exist as enantiomers and diastereomers. In particular if the carbon atom of the piperidine ring to which the diphenyl$(C_{1-2})$alkylene group (i.e. the $(Ph_2)(Ph_3)CH(CH_2)_q$—group) is attached is at the 2 or 3-position in relation to the nitrogen then this carbon atom is an asymetric center. Moreover, when $Ph_2$ and $Ph_3$ are not identical, the carbon atom to which these phenyl groups are attached is an asymmetric center. References to the compounds of formula 1, or any intermediate thereof, may therefore be construed as covering a specific optical isomer, a racemic mixture or a diastereomeric mixture. The specific optical isomers can be synthesized or can be separated and recovered by techniques known in the art such as chromatography on chiral stationary phases, resolution via chiral salt formation and subsequent separation by selective crystallization, as is known in the art. Alternatively, a chirally pure starting material may be utilized.

The expression "a pharmaceutically acceptable acid addition salt" is intended to apply to any non-toxic organic or inorganic acid addition salt of the base compounds. Illustrative inorganic acids which form suitable salts include hydrochloric, hydrobromic, sulfuric, and phosphoric acids and acid metal salts such as sodium monohydrogen orthophosphate and potassium hydrogen sulfate. Illustrative organic acids which form suitable salts include the mono, di, and tricarboxylic acids. Illustrative of such acids are, for example, acetic, glycolic, lactic, pyruvic, malonic, succinic, glutaric, fumaric, malic, tartaric, citric, ascorbic, maleic, hydroxymalic, benzoic, hydroxybenzoic, phenylacetic, cinnamic, and 2-phenoxybenzoic acids. Other organic acids which form suitable salts are the sulfonic acids such as methane sulfonic acid and 2-hydroxyethane sulfonic acid. These salts and the base compounds can exist in either a hydrated or a substantially anhydrous form. The acid salts are prepared by standard techniques such as by dissolving the free base in aqueous or aqueous-alcohol solution or other suitable solvent containing the appropriate acid and isolating by evaporating the solution, or by reacting the free base in an organic solvent in which case the salt separates directly or can be obtained by concentration of the solution or in a solvent such as water which is then removed in vacuo or by freeze-drying, or by exchanging the cations of an existing salt for another cation on a suitable ion exchange resin. In general the acid addition salts of the compounds of this invention are crystalline materials which are soluble in water and various hydrophilic organic solvents and which in comparison to their free base forms, demonstrate higher melting points and an increased solubility.

As is true for most classes of therapeutically effective compounds, certain subclasses and certain species are especially effective and are preferred over others. In this instance, those compounds of Formula 1 wherein $Ph_1$ is an unsubstituted phenyl or is a phenyl substituted with one or two alkoxy groups are preferred. More preferred are those formula 1 compounds wherein n is the integer 2, as well as those compounds of formula 1 wherein $Ph_1$ is a phenyl group substituted with one or two methoxy groups. Most preferred is the compound of formula 1 wherein n is the integer 2, m is the integer 1, q is the integer 1, $Ph_1$ is a 3,4-dimethoxyphenyl group and wherein $Ph_2$ and $Ph_3$ are each an unsubstituted phenyl group.

Applicants have prepared compounds of formula 1 as illustrated in scheme 1 by reacting a suitably substituted 2-,3-, or 4- diphenylalkyl substituted cyclic amine of formula 2 with a suitably substituted phenylalkylcarbonylchloride of formula 3. The resulting amide of formula 4 is then reduced by, for example, treatment with diborane to yield the desired product of formula 1.

Alternatively, the compounds of formula 1 can be made as illustrated in scheme 2 by direct alkylation of a suitably substituted 2-,3-, or 4- diphenylalkyl substituted cyclic amine of formula 2 with a suitably substituted aralkyl halide of formula 5. Further illustrations of the preparation of the compounds of this invention are provided in the examples.

SCHEME 1

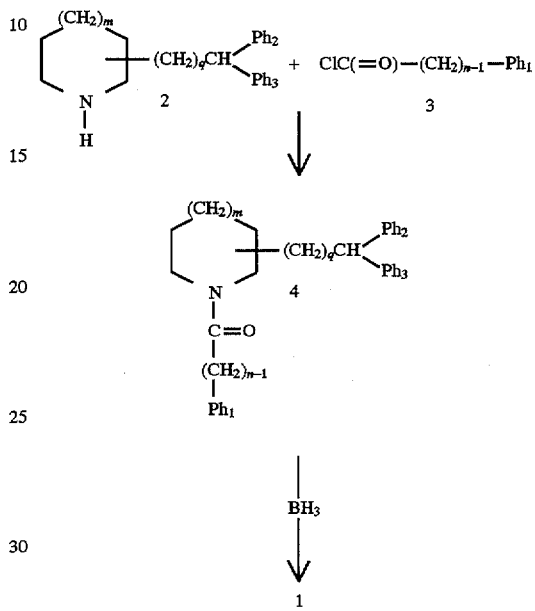

SCHEME 2

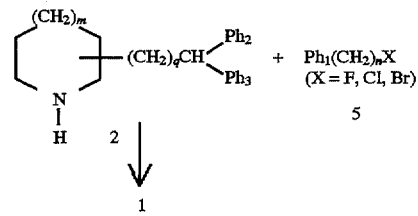

The ability of the triphenylpiperidines derivatives of this invention to reverse drug resistance in multi-drug resistant tumors can be demonstrated by the ability of test compounds to reduce cell growth in a vinblastine (VBL) resistant tumor cell line.

The ability of compounds of this invention to reverse multi drug resistance can be determined using standard test procedures. The ability of the test compounds to inhibit the growth of multidrug resistant human epidermoid carcinoma (KBV1) cells in the presence of both Vinblastine and the compound was determined. These cells are at least 1,000 times resistant to vinblastine compared to wild type KB cells. Vinblastine (0.25 µg/ml) alone showed 0–10% growth inhibition. Compound alone at different concentrations did not significantly inhibit any growth of KBV1 cells. The results are tabulated in Table 1.

TABLE 1

MODULATION OF DRUG RESISTANCE IN HUMAN
EPIDERMOID CARCINOMA (KBV1) CELLS
BY 1-(3,4-DIMETHOXYPHENETHYL-2-(2,2-
DIPHENYLETHYL)PIPERIDINE

| Concentration (μM) | % Inhibition of Growth | |
|---|---|---|
| | Compound Alone | Compound + VLB* |
| 0.23 | 12.2 | 94.2 |
| 0.18 | 8.1 | 91.6 |
| 0.12 | 0 | 60.0 |
| 0.06 | 1.0 | 30.4 |

*VLB at 0.25 μg/ml showed 0–10% growth inhibition.

The term "patient" used herein is taken to mean mammals such as primates, including humans, sheep, horses, cattle, pigs, dogs, cats, rats and mice.

The amount of the triphenylpiperidine derivative of formula 1 to be administered can vary widely according to the particular dosage unit employed, the period of treatment, the age and sex of the patient treated, the nature and extent of the multidrug resistance in the tumor to be treated, and the particular triphenylpiperidine derivative selected. The triphenylpiperidine derivative is used in conjunction with other chemotherapeutic agents known to be useful in the treatment of tumors. The amount of a triphenylpiperidine derivative of formula 1 effective to reverse multidrug resistance will generally range from about 15 mg/kg to 500 mg/kg. A unit dosage may contain from 25 to 500 mg of the triphenylpiperidine derivative, and can be taken one or more times per day. The triphenylpiperidine derivative can be administered with a pharmaceutical carrier using conventional dosage unit forms either orally or parenterally.

Treatment of tumors by the method of this invention requires that an anti-tumor effective amount of a chemotherapeutic agent be administered together with a compound of formula 1. Tumors which can be treated by the method of this invention include both benign and malignant tumors or neoplasms, and include melanomas, lymphomas, leukemias, and sarcomas. Illustrative examples of tumors are cutaneous tumors, such as malignant melanomas and mycosis fungoides; hematologic tumors such as leukemias, for example, acute lymphoblastic, acute myelocytic or chronic myelocytic leukemia; lymphomas, such as Hodgkin's disease or malignant lymphoma; gynecologic tumors, such as ovarian and uterine tumors; urologic tumors, such as those of the prostate, bladder or testis; soft tissue sarcomas, osseus or non-osseus sarcomas, breast tumors; tumors of the pituitary, thyroid and adrenal cortex; gastrointestinal tumors, such as those of the esophagus, stomach, intestine and colon; pancreatic and hepatic tumors; laryngeae papillomestasas and lung tumors. Of course those tumors which typically are or become multi-drug resistant are most beneficially treated with the method of this invention. Such tumors include colon tumors, breast tumors, lung tumors, stomach tumors, and liver tumors.

The chemotherapeutic agents used together with the triphenylpiperidines of formula I are those cytotoxic agents commonly used in the treatment of tumors. Illustrative examples of chemotherapeutic agents are: cyclophosphamide, methotrexate, prednisone, 6-mercaptopurine, procarbazine, daunorubicin, vincristine, vinblastine, chlorambucil, cytosine arabinoside, 6-thioguanine, thio TEPA, 5-fluorouracil, 5-fluoro-2-deoxyudirinde, 5-azacytidine, nitrogen mustard, 1,3-bis(2-chloroethyl)-1-nitrosourea (BCNU), (1-(2-chloroethyl)-3-cyclohexyl-1-nitrosourea) (CCNU), busulfan, adriamycin, bleomycin, vindesine, cycloleucine or methylglyoxal bix (guanylhydrazone) (i.e., MGBG). The effective amount of chemotherapeutic agent used in the method of this invention varies widely and depends on factors such as the patient, the tumor tissue type and its size, and the particular chemotherapeutic agent selected. The amount is any effective amount and can be readily determined by those skilled in the art. In general, less chemotherapeutic agent will be required when administered with the triphenylpiperidine of formula 1, primarily because the problem of drug resistance need not addressed by the addition of larger quantities of chemotherapeutic agent. Of course mixtures of chemotherapeutic agents may be employed and surgical excision and radiation therapy may be useful adjuvants as in any tumor therapy. While the compound of formula 1 and the chemotherapeutic agent are said to be administered together, this does not necessarily mean that the compounds are formulated into the same dosage form or are administered concurrently. Rather, the expression "together" means that a compound of formula 1 and the chemotherapeutic agent(s) are administered in a combined dosage form or separately during the course of therapy.

The preferred route of administration is oral administration. For oral administration the triphenylpiperidinederivative can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The triphenylpiperidine derivatives of this invention may also be administered parenterally, that is, subcutaneously, intravenously, intramuscularly, or intraperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkylbeta-aminopropionates, and 2-alkylimidazoline quarternary ammonium salts, as well as mixtures. The parenteral compositions of this invention will typically contain from about 0.5 to about 25% by weight of the oxazolone derivative of formula 1 in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. An least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

The following specific examples are presented to illustrate the synthesis of the compounds of this invention. Note that Examples 1, 3–7, 11, 13–16, 21 and 22 are intermediates not within the scope of the claims.

EXAMPLE 1

1-(3,4-Dimethoxyphenylacetyl)-2-(2,2-diphenylethyl)piperidine

A solution of 2.65 g (0.01M) of 2-(2,2-diphenylethyl) piperidine in 25 ml of methylene chloride containing 1.5 ml of triethylamine was cooled in ice and a solution of 2.35 g (0.011M) of 3,4-di-methoxyphenylacetyl chloride in 25 ml of methylene chloride was added dropwise. The cooling bath was removed and the mixture was stirred at room temperature overnight. The mixture was then washed with dilute hydrochloric acid, water, dilute sodium hydroxide and saturated sodium chloride solution. Removal of the solvent left an oil which was purified by chromatography on silica gel. The solid thus obtained melted at 113°–114° C. after recrystallization from cyclohexane-ethyl acetate.

Anal. Calcd for $C_{29}H_{33}NO_3$: C=78.52; H=7.50; N=3.16 Fd.: C=78.38; H=7.59; N=2.96

EXAMPLE 2

1-(3,4-Dimethoxyphenethyl)-2-(2,2-diphenylethyl) piperidine Maleate

A solution of 4.43 g (0.01M) of 1-(3,4-dimethoxyphenylacetyl)-2-(2,2-diphenylethyl)piperidine in 50 ml of tetrahydrofuran was treated with 10 ml of 2M borane-methyl sulfide and the mixture was refluxed for 3 hours. After evaporation of the solvent, 10 ml of methanol was added followed by 15 ml of 6N hydrochloric acid. The solution was heated on the steam bath for 1 hour and the methano was removed at reduced pressure. After basification with sodium hydroxide solution, the water-insoluble product was extracted into ether. Treatment of the extract with an ethereal solution of maleic acid gave the salt, m.p. 105°–108° C.

Anal. Calcd for $C_{29}H_{35}NO_2.C_4H_4O_4$: C=72.64; H=7.20; N=2.57 Fd.: C=72.34; H=7.17; N=2.51

Additionally, the compounds of examples 3–20 were similarly prepared.

EXAMPLE 3

1-(3,4,5-trimethoxyphenylacetyl)-2-(2,2-diphenylethyl)piperidine

Anal., Calcd for $C_{30}H_{35}NO_4$: C=76.08; H=7.45; N=2.96 Fd.: C=75.96; H=7.46; N=2.89 m.p. 105°–106°

EXAMPLE 4

1-(3,4-dichlorophenylacetyl)-2-(2,2-diphenylethyl)
piperidine

Anal., Calcd for $C_{27}H_{27}Cl_2NO$: C=71.68; H=6.02; N=3.10 Fd.: C=71.60; H=6.16; N=3.04 m.p. 82°–84°

EXAMPLE 5

1-(3,4-dimethoxyphenylpropionyl)-2-(2,2-diphenylethyl)piperidine

Anal., Calcd for $C_{30}H_{35}NO_3$: C=78.74; H=7.71; N=3.06 Fd.: C=78.49; H=7.86; N=2.87 m.p. 138°–139°

EXAMPLE 6

1-(3,4,5-trimethoxyphenylacetyl)-2-[2,2-bis-(4-methylphenyl)ethyl]piperidine

Anal., Calcd for $C_{32}H_{39}NO_4$: C=76.62; H=7.84; N=2.79 Fd.: C=76.38; H=7.84; N=2.71 m.p. 98°–100°

EXAMPLE 7

1-(2-methoxyphenylacetyl)-2-(2,2-diphenylethyl)
piperidine,

Anal., Calcd for $C_{28}H_{31}NO_2$: C=81.32; H=7.56; N=3.39 Fd.: C=80.57; H=7.51; N=3.28 an oil

EXAMPLE 8

1-(3,4,5-trimethoxyphenethyl)-2-(2,2-diphenylethyl)
piperidine fumarate

Anal., Calcd for $C_{30}H_{37}NO_3.C_4H_4O_4$: C=70.93; H=7.18; N=2.43 Fd.: C=70.42; H=7.16; N=2.82 m.p. 174°–176°

EXAMPLE 9

1-(3,4-dimethoxybenzyl)-2-(2,2-diphenylethyl)
piperidine oxalate

Anal., Calcd for $C_{28}H_{33}NO_2.C_2H_2O_4$: C=71.26; H=6.98; N=2.77 Fd.: C=70.98; H=7.20; N=2.80 m.p. 140°–143°

EXAMPLE 10

1-(3,4-dimethoxyphenylpropyl)-2-(2,2-diphenylethyl)piperidine fumarate

Anal., Calcd for $C_{30}H_{37}NO_2.C_4H_4$: C=72.96; H=7.38; N=2.50 Fd.: C=72.69; H=7.38; N=2.50 m.p. 111°–113°

EXAMPLE 11

1-(3,4-dimethoxybenzoyl)-2-(2,2-diphenylethyl)
piperidine

EXAMPLE 12

1-(3,4-dichlorophenethyl)-2-(2,2-diphenylethyl)
piperidine

EXAMPLE 13

1-Benzoyl-2-[(bis-3-chlorophenyl)ethyl]piperidine

EXAMPLE 14

1-(3,4-dimethoxyphenylacetyl)-2-(diphenylmethyl)
piperidine

EXAMPLE 15

1-(3,4-dimethoxyphenylpropionyl)-3-(2,2-diphenylethyl)piperidine

EXAMPLE 16

1-(3,4,5-trimethoxyphenylpropionyl)-4-[bis-(4-fluorophenyl)methyl]piperidine

EXAMPLE 17

1-Benzyl-2-[(bis-3-chlorophenyl)ethyl]piperidine
(fumarate)

EXAMPLE 18

1-(3,4-dimethoxyphenethyl)-2-(diphenylmethyl)
piperidine(fumarate)

EXAMPLE 19

1-(3,4-dimethoxyphenylpropyl)-3-(2,2-diphenyl)
ethylpiperidine(fumarate)

EXAMPLE 20

1-(3,4,5-trimethoxyphenylpropyl)-4-[bis-(4-fluorophenyl)methyl]piperidine(fumarate)

EXAMPLE 21

1-(3,4-dimethoxylphenylacetyl-2-(2,2-diphenylethyl)
pyrrolidine

EXAMPLE 22

1-(3,4,5-trimethoxylphenylpropionyl)-2-(2,2-diphenylethyl)azepine

EXAMPLE 23

1-(3,4-dimethoxyphenethyl)-2-(2,2-diphenylethyl)
pyrrolidine(fumarate)

EXAMPLE 24

1-(3,4,5-trimethoxyphenylpropyl)-2-(2,2-biphenylethyl)azepine

What is claimed is:

1. A method of reversing multidrug resistance in a patient having a multidrug resistant tumor which comprises administering to the patient a nontoxic multidrug resistance reversing amount of a compound of the formula

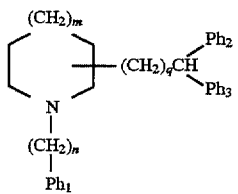

wherein $Ph_1$ is a phenyl substituted with one or two $(C_1-C_4)$alkoxy groups;

$Ph_2$, and $Ph_3$ are each a phenyl group;

n is an integer 2;

m is an integer 1; and q is an integer of from 1 to 2;

or an acid addition salt thereof.

2. A method according to claim 1 wherein the compound is 1-(3,4-Dimethoxyphenethyl)-2-(2,2-diphenylethyl) piperidine Maleate.

3. A compound that is selected from the group consisting of 1-(3,4-Dimethoxyphenylacetyl)-2-(2,2-diphenylethyl) piperidine;

1-(3,4,5-trimethoxyphenylacetyl)-2-(2,2-diphenylethyl) piperidine;

1-(3,4-dichlorophenylacetyl)-2-(2,2-diphenylethyl) piperidine;

1-(3,4-dimethoxyphenylpropionyl)-2-(2,2-diphenylethyl) piperidine;

1-(3,4,5-trimethoxyphenylacetyl)-2-[2,2-bis-(4-methylphenyl)ethyl]piperidine; and 1-(2-methoxyphenylacetyl)-2-(2,2-diphenylethyl) piperidine.

4. A compound of claim 3 wherein said compound is 1-(3,4-Dimethoxyphenylacetyl)-2-(2,2-diphenylethyl) piperidine.

* * * * *

UNITED STATES PATENT AND TRADEMARK OFFICE
CERTIFICATE OF CORRECTION

PATENT NO. : 5,670,521
DATED : September 23, 1997
INVENTOR(S) : Jules Freedman and Sai P. Sunkara It is certified that error appears in the above-identified patent and that said Letters Patent is hereby corrected as shown below:

At column 7, line 2, the patent reads "pharmaceutically adjuvants" and should read --pharmaceutical adjuvants--.
At column 8, line 2, the patent reads "An least" and should read --At least--.
At column 8, line 48, the patent reads "methano" and should read --methanol--.
At column 12, claims 3 and 4 were deleted by amendment and should not appear on the patent.

Signed and Sealed this

First Day of September, 1998

Attest:

BRUCE LEHMAN

Attesting Officer

Commissioner of Patents and Trademarks